United States Patent
Schmidtke et al.

(10) Patent No.: US 7,825,281 B2
(45) Date of Patent: Nov. 2, 2010

(54) METHOD FOR PRODUCING ELECTRONIC GRADE 2,2'-AMINOETHOXYETHANOL

(75) Inventors: Helmut Schmidtke, Bensheim (DE);
Martin Rudloff, Gönnheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 27 days.

(21) Appl. No.: 12/443,226

(22) PCT Filed: Sep. 21, 2007

(86) PCT No.: PCT/EP2007/060017

§ 371 (c)(1),
(2), (4) Date: Mar. 27, 2009

(87) PCT Pub. No.: WO2008/037659

PCT Pub. Date: Apr. 3, 2008

(65) Prior Publication Data

US 2010/0029989 A1    Feb. 4, 2010

(30) Foreign Application Priority Data

Sep. 28, 2006    (EP) .................................. 06121405

(51) Int. Cl.
*C07C 209/16* (2006.01)
(52) U.S. Cl. ..................... 564/474; 564/477; 564/479; 564/480; 564/497
(58) Field of Classification Search ........................ None
See application file for complete search history.

(56) References Cited

U.S. PATENT DOCUMENTS

| 5,288,911 A | 2/1994 | Koppenhoefer et al. |
| 7,183,438 B2 | 2/2007 | Gerlach et al. |
| 2008/0255351 A1 | 10/2008 | Hoffer et al. |

FOREIGN PATENT DOCUMENTS

| EP | 0510382 A2 | 10/1992 |
| WO | WO-03/076386 A2 | 9/2003 |
| WO | WO-2007/036496 A1 | 4/2007 |
| WO | WO 2008/037587 A1 | 4/2008 |
| WO | WO 2008/037589 A1 | 4/2008 |
| WO | WO 2008/037590 A1 | 4/2008 |

OTHER PUBLICATIONS

Database CAPLUS on STN, Acc. No. 1977:75586, Koliushko et al., Gazovaya Promyshlennost (1976), 8, p. 25-27 (abstract).*

* cited by examiner

*Primary Examiner*—Brian J Davis
(74) *Attorney, Agent, or Firm*—Connolly Bove Lodge & Hutz LLP

(57) ABSTRACT

A process for preparing electronics-grade 2,2'-aminoethyoxyethanol by reacting diethylene glycol with ammonia in the presence of a catalyst in a reactor to give a reaction mixture from which a crude 2,2'-aminoethoxyethanol stream is separated off and is purified further by distillation in a pure column, wherein a sidestream comprising electronics-grade 2,2'-aminoethoxyethanol is taken off from the pure column as a result of the diethylene glycol being passed through a filter which ensures a degree of removal of at least 99% for solid particles having a maximum particle size of $\leq 1.5$ µm before the diethylene glycol is fed into the reactor, is proposed.

8 Claims, No Drawings

METHOD FOR PRODUCING ELECTRONIC GRADE 2,2'-AMINOETHOXYETHANOL

RELATED APPLICATIONS

This application is a national stage application (under 35 U.S.C. §371) of PCT/EP2007/060017, filed Sep. 21, 2007, which claims benefit of European Application No. 06121405.2, filed Sep. 28, 2006.

The invention relates to a process for preparing electronics-grade 2,2'-amino-ethoxyethanol (hereinafter referred to as ADG for short). ADG is prepared by reacting diethylene glycol with ammonia in the presence of a catalyst. Morpholine is formed as coproduct. The reaction mixture is generally fractionally distilled in a plurality of stages, with an ADG-comprising stream and a morpholine-comprising stream being obtained after ammonia, water and secondary components have been separated off.

The purification of the ADG-comprising stream by distillation is carried out in a sidesteam column in which low-boiling secondary components are separated off at the top and high-boiling secondary components are discharged in the bottoms from the column. Pure ADG having an ADG content of at least 98.0% by weight is obtained as sidestream.

The apparatuses in the plant for obtaining pure ADG (in particular reactors and separation columns) generally comprise austenitic stainless steels, in particular those having the material numbers 1.4541 and 1.4571.

However, for electronics applications, for example for cleaning circuit boards, pure ADG has to meet specific specification requirements with regard to the permissible residue contents of metals. Electronics-grade ADG typically has to meet the following specifications:

ADG content: min. 98.00% by weight, diethylene glycol content: max. 0.40% by weight, water content: max. 0.20% by weight (determined by the Karl Fischer method in accordance with DIN 51777), color number: max. 20 APHA (in accordance with DIN EN 1557), a maximum content of aluminum, arsenic, gold, boron, calcium, cadmium, cobalt, chromium, copper, potassium, magnesium, manganese, nickel, antimony, tin and titanium of 20 ppb each and a maximum content of iron, sodium and zinc of 30 ppb each, in each case determined by ICP-MS (inductively coupled plasma mass spectrometry).

However, it has been found that the above specifications cannot be achieved reliably in the production of ADG under conventional process conditions. There are particular restrictions in the processing of diethylene glycol which becomes contaminated beforehand, for example during storage and transport, with more than 50 ppb of the abovementioned metal ions.

It was therefore an object of the invention to provide a process by means of which electronics-grade ADG can be obtained in existing plants without extensive, costly additional measures in terms of apparatus and/or process engineering. In particular, no changes in the reaction of the starting material over the catalyst and the intermediate distillation steps should have to be made.

This object is achieved by a process for preparing electronics-grade ADG by reacting diethylene glycol with ammonia in the presence of a catalyst in a reactor to give a reaction mixture from which a crude 2,2'-ADG stream is separated off and is purified further by distillation in a pure column, wherein a sidestream comprising electronics-grade ADG is taken off from the pure column as a result of the diethylene glycol being passed through a filter which ensures a degree of removal of at least 99% for solid particles having a maximum particle size of $\leq 1.5$ μm before the diethylene glycol is fed into the reactor.

The diethylene glycol feed to the production plant can, in particular become contaminated with metal ions during preceding production steps, storage and transport, typically with impurities in a concentration of up to 2000 μg/l, or 400 μg/l or from 0 to 100 μg/l.

The inventors have recognized that a significant improvement in respect of the residue content of components harmful to the specification, in particular cations, in the ADG is possible when a high-performance filter which is suitable for removing solid particles having a maximum particle size of $\leq 1.5$ μm, preferably a maximum particle size of $\leq 1$ μm, is installed in the feed line for diethylene glycol leading into the reactor.

Particular preference is given to a filter whose removal behavior can be characterized by the following parameters:

The degree of removal achieved for solid particles having a maximum particle size of 0.2 μm is at least 60%, the degree of removal achieved for solid particles having a maximum particle size of 0.6 μm is at least 90%, the degree of removal achieved for solid particles having a maximum particle size of 0.8 μm is at least 95%, the degree of removal achieved for solid particles having a maximum particle size of 1.5 μm is at least 99% and the degree of removal achieved for solid particles having a maximum particle size of 5.0 μm is at least 99.98%.

To characterize the removal behavior, the maximum particle size can be determined, for example, by means of static light scattering.

As filter, preference is given to using a bag filter made of polypropylene, in particular one having a volume of from 30 to 40 l, in particular 32 l, which is installed in a separation vessel and through which the diethylene glycol flows from the top downward. The impurities are retained on the inside of the filter.

In a preferred embodiment, the filtration of the diethylene glycol starting material fed to the synthesis is supplemented by selection of particular operating conditions in the column used for the purification of the ADG by distillation, which is located at the end of the process chain. In this column, the distilled electronics-grade ADG is taken off in the liquid state as a sidestream, while the organic secondary components having a boiling point of >235° C. (at 1.013 bar) are discharged in the bottoms and the organic compounds having a boiling point of <222° C. (at 1.013 bar) are discharged at the top of the column. The column is preferably operated at a pressure of from 0.005 to 0.2 bar.

The point at which the ADG-comprising stream is fed in is, based on the theoretical plates, above the middle of the column. The liquid side offtake for the pure product located on the opposite side is from 1 to 30 theoretical plates, in particular cases from 10 to 25 theoretical plates, above the feed point in the enrichment section of the column.

In the process of the invention, the separation stages located between the inlet for the crude ADG stream and the offtake for the sidestream comprising electronics-grade ADG are preferably operated at an increased liquid loading $w_L$ compared to known processes (at an otherwise constant velocity of the ascending vapor). The liquid loading $w_L$ is the ratio of the volume flow of the liquid trickling down onto the separation stages $\dot{V}_L$ to the free cross-sectional area A of the separation stages. The liquid loading $w_L$ has the dimensions of a velocity $$w_L[m/s] = \dot{V}_L[m^3/s]/A[m^2]$$

The velocity of the ascending vapor $w_D$ is derived from the mass flow of the vapor condensed at the top of the column $\dot{m}_L$, the density of the vapor $\rho_D$ and the free cross-sectional area A of the separation stages:

$$w_D[m/s] = \dot{m}_L[kg/s]/\rho_D[kg/m^3]/A[m^2]$$

In the process of the invention, the metallic impurities introduced via the starting material to the production plants and still present in relatively high proportions in the feed to the pure column were able to be kept out of the product at an increased ratio of liquid loading $w_L$ to vapor velocity $w_D$ of preferably $w_L/w_D > 0.160$, in particular cases $w_L/w_D > 0.170$.

The process is particularly preferably operated with recirculation:

here, the diethylene glycol which has not been converted into desired product in the process is taken off at the bottom of the pure ADG column and mixed into the fresh feedstream comprising crude ADG upstream of the filter. This mode of operation of the process allows increased removal of metallic impurities, in particular after shutting down the plant during which additional impurities are introduced into the otherwise closed system as a result of the opening of plant components.

EXAMPLES

The process of the invention was used under the abovementioned conditions in continuous operation in a production plant.

A pure ADG column which had 44 theoretical plates and in which 9 theoretical plates were located between the point at which the feedstream comprising crude ADG was fed in and the offtake for the sidestream comprising pure electronics-grade ADG was used. The ratio of liquid loading and vapor velocity was varied for the theoretical plates between the point at which the feedstream was fed in and the offtake for the sidestream and the influence of this and also the influence of the use of a filter in the feed path on the residual iron concentration in the product was examined.

Examples 1 to 3

A feedstream comprising diethylene glycol comprising 300 ppb of iron was used.

Example 1

The ratio of liquid loading and vapor velocity was set to a value of 0.165. The process was operated without mechanical filters in the feed path.

The product stream comprising pure ADG had an iron concentration of 50 ppb.

Example 2

The process was operated in a manner analogous to Example 1, likewise without mechanical filters in the feed path but at a ratio of the liquid loading to vapor velocity of 0.185.

The residual iron concentration in the ADG product stream was 27 ppb.

Example 3

The process was operated in a manner analogous to Examples 1 and 2, but at a ratio of liquid loading to vapor velocity of 0.183 and additionally with a mechanical high-performance filter in the feed path, namely a bag filter made of polypropylene having a volume of 32 l and the following removal characteristics:

a degree of removal of solid particles having a maximum particle size of 0.2 µm of at least 60%, a degree of removal of solid particles having a maximum particle size of 0.6 µm of 90%, a degree of removal of solid particles having a maximum particle size of 0.8 µm of at least 95%, a degree of removal of solid particles having a maximum particle size of 1.5 µm of at least 99% and a degree of removal of solid particles having a maximum particle size of 5.0 µm of at least 99.98%.

The concentration of iron in the pure ADG was in this case 9 ppb.

Examples 4 to 6

Examples 4 to 6 were carried out at an iron concentration in the feedstream of 345 ppb. In all the Examples 4 to 6, a mechanical high-performance filter corresponding to the description for Example 3 above was installed in the flow path.

Examples 4 to 6 are distinguished by different values of the ratio of liquid loading to vapor velocity under otherwise unchanged operating conditions.

Example 4

The ratio of liquid loading to vapor velocity was 0.178. A residual concentration of iron in the pure ADG of 7 ppb was achieved here.

Example 5

The ratio of liquid loading to vapor velocity was 0.155, corresponding to the mode of operation in the prior art. The residual iron contamination in the pure ADG was able to be limited to 28 ppb by use of the high-performance filter in the feed path.

Example 6

The ratio of liquid loading to vapor velocity was set to 0.175. The residual iron contamination in the pure ADG stream was 8 ppb.

The invention claimed is:

1. A process for preparing electronics-grade 2,2'-aminoethyoxyethanol comprising reacting diethylene glycol with ammonia in the presence of a catalyst in a reactor to give a reaction mixture from which a crude 2,2'-aminoethoxyethanol stream is separated off and is purified further by distillation in a pure column, wherein a sidestream comprising electronics-grade 2,2'-aminoethoxyethanol is taken off from the pure column as a result of said diethylene glycol being passed through a filter which ensures a degree of removal of at least 99% for solid particles having a maximum particle size of less than or equal to 1.5 µm before the diethylene glycol is fed into the reactor.

2. The process of claim 1, wherein the diethylene glycol is passed through a filter which ensures a degree of removal of at least 99% for solid particles having a maximum particle size of less than or equal 1.0 µm.

3. The process of claim 1, wherein said filter is a bag filter made of polypropylene.

4. The process of claim 1, wherein said sidestream comprising electronics-grade 2,2'-amino-ethoxyethanol is taken off from the pure column at a location from 1 to 30 theoretical plates above the point where the crude 2,2'-aminoethoxyethanol stream is fed into the pure column and the separation stages located between the point where the crude 2,2'-aminoethoxyethanol stream is fed into the pure column and where the sidestream comprising electronics-grade 2,2'-aminoethoxyethanol is taken off from the pure column are operated at a ratio of liquid loading to vapor velocity of greater than 0.160.

5. The process of claim 4, wherein said separation stages are operated at a ratio of liquid loading to vapor velocity of greater than 0.170.

6. The process of claim 1, further comprising taking off a bottom stream from the pure column and mixing said bottom stream into said crude 2,2'-aminoethoxyethanol upstream of said filter.

7. The process of claim 4, wherein said sidestream comprising electronics-grade 2,2'-amino-ethoxyethanol is taken off from the pure column at a location from 15 to 25 theoretical plates above the point where the crude 2,2'-aminoethoxyethanol stream is fed into the pure column.

8. The process of claim 5, wherein said sidestream comprising electronics-grade 2,2'-amino-ethoxyethanol is taken off from the pure column at a location from 15 to 25 theoretical plates above the point where the crude 2,2'-aminoethoxyethanol stream is fed into the pure column.

* * * * *